Figure 1:
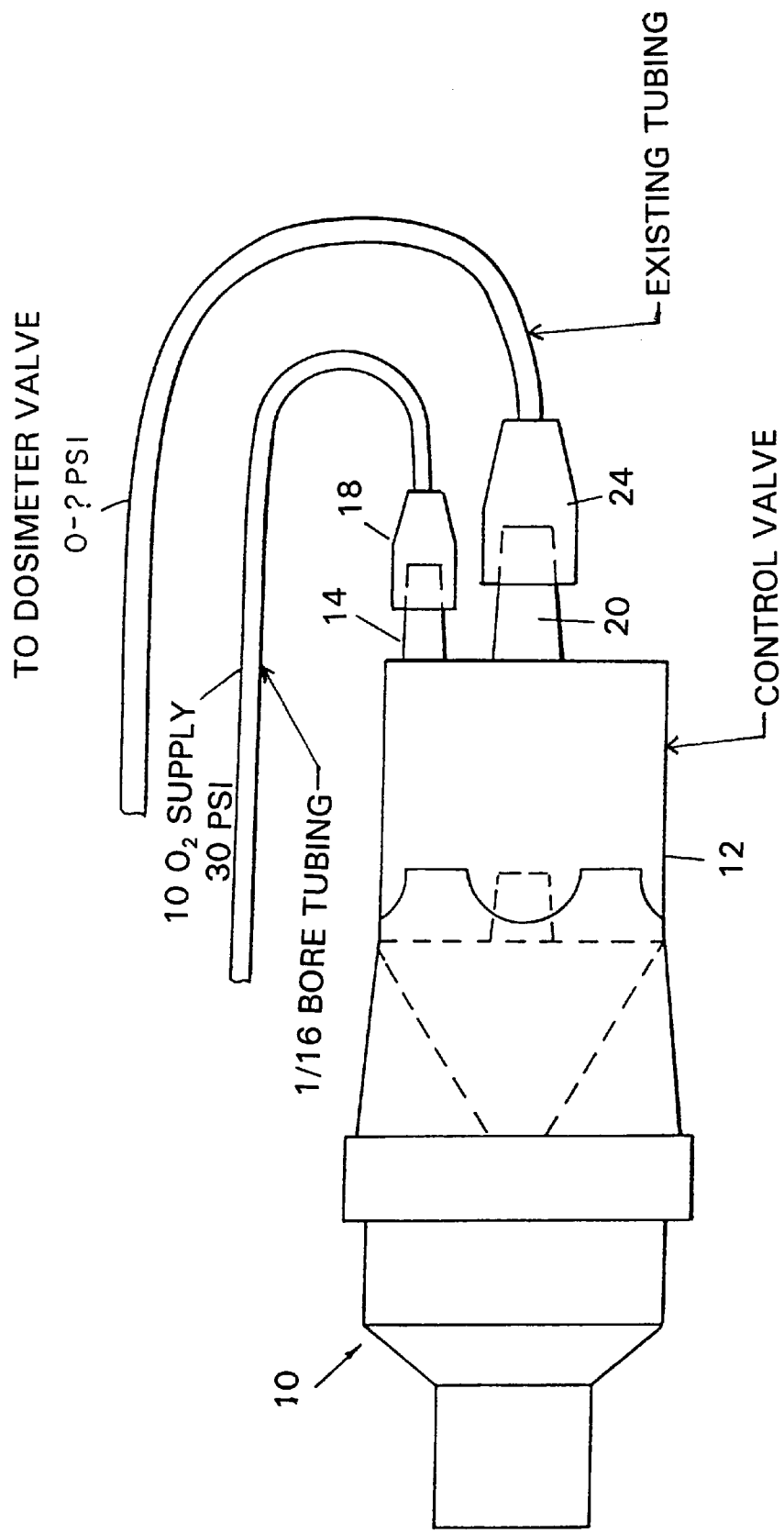
Figure 2:
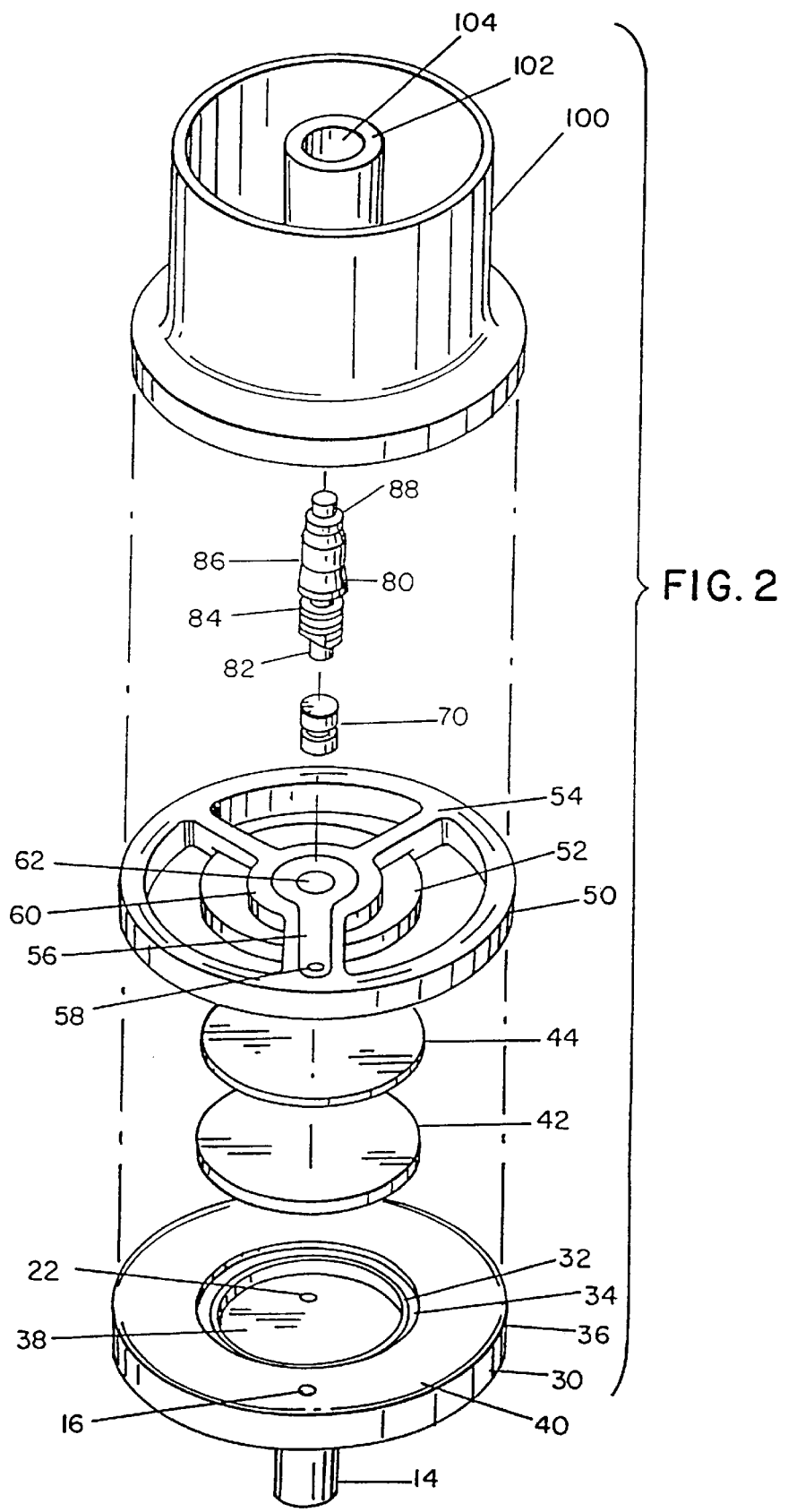

United States Patent [19]
Davenport et al.

[11] Patent Number: 6,105,929
[45] Date of Patent: Aug. 22, 2000

[54] CONTROL VALVE FOR GAS SUPPLY TO A NEBULIZER

[75] Inventors: James Davenport, Fallbrook; James Chua, Bakersfield, both of Calif.

[73] Assignee: Salter Labs, Arvin, Calif.

[21] Appl. No.: 09/166,160

[22] Filed: Oct. 5, 1998

Related U.S. Application Data

[60] Provisional application No. 60/065,792, Nov. 14, 1997.

[51] Int. Cl.[7] .................................................. F16K 31/12
[52] U.S. Cl. ........................ 251/63.6; 251/61.4; 251/63.4
[58] Field of Search ................... 251/61.4, 63.4, 251/63.6

[56] References Cited

U.S. PATENT DOCUMENTS

| | | | |
|---|---|---|---|
| 960,986 | 6/1910 | Moore | 251/63.4 X |
| 1,249,293 | 12/1917 | Norwood | 251/61.4 X |
| 2,230,914 | 2/1941 | Sherman | 251/61.4 |
| 2,470,296 | 5/1949 | Fields | 128/266 |
| 3,048,274 | 8/1962 | Lundeen | 251/61.4 X |
| 3,195,854 | 7/1965 | Pflieger | 251/61.4 |
| 3,414,014 | 12/1968 | Merchant et al. | 137/559 |
| 3,623,694 | 11/1971 | Goldberg | 251/61.4 |
| 3,870,046 | 3/1975 | Elliott | 128/266 |
| 4,040,440 | 8/1977 | Zaki | 137/375 |
| 4,214,727 | 7/1980 | Baram | 251/63.4 |
| 4,276,876 | 7/1981 | Häkkinen | 128/200 |
| 4,421,292 | 12/1983 | Matsui et al. | 251/63.4 X |
| 4,456,016 | 6/1984 | Nowacki et al. | 128/725 |
| 4,534,343 | 8/1985 | Nowacki et al. | 128/200.23 |
| 4,598,704 | 7/1986 | Bordoni et al. | 128/200.14 |
| 4,697,587 | 10/1987 | Marinkovich | 128/203.11 |
| 4,703,753 | 11/1987 | Bordoni et al. | 128/200.14 |
| 4,805,609 | 2/1989 | Roberts et al. | 128/200.21 |
| 4,832,012 | 5/1989 | Raabe et al. | 128/200.21 |
| 4,938,209 | 7/1990 | Fry | 128/200.21 |
| 5,040,527 | 8/1991 | Larson et al. | 128/200.23 |
| 5,080,093 | 1/1992 | Raabe et al. | 128/203.12 |
| 5,086,765 | 2/1992 | Levine | 128/200.21 |
| 5,113,855 | 5/1992 | Newhouse | 128/203.12 |
| 5,119,807 | 6/1992 | Roberts | 128/200.24 |
| 5,570,682 | 11/1996 | Johnson | 128/200.14 |
| 5,584,285 | 12/1996 | Salter et al. | 128/200.21 |
| 5,829,473 | 11/1998 | Hajbi et al. | 251/61.4 X |

*Primary Examiner*—Kevin Shaver
*Assistant Examiner*—John Bastianelli
*Attorney, Agent, or Firm*—Davis and Bujold

[57] ABSTRACT

A pilot valve permits the delivery of relatively high pressure gas on the order of 30–50 psi directly to the valve. A poppet valve is positioned in the outlet gas delivery tube of the valve housing and has a valve stem which is spring loaded to maintain the valve in the closed position and a high pressure gas is supplied to the poppet valve. A trigger gas in the form of a low pressure gas is supplied to the pilot valve to cause the pilot valve to open. A poppet valve opening mechanism responds to the presence of the trigger gas to move the valve stem of the poppet valve to open the poppet valve and to permit the high pressure gas to pass through the poppet valve and through the pilot valve. A preferred opening mechanism is a diaphragm which moves in response to the trigger gas and causes a backup disk to also move and force a piston against the valve stem of the poppet valve.

3 Claims, 3 Drawing Sheets

CONTROL VALVE FOR GAS SUPPLY TO A NEBULIZER

This application claims Provisional Application 60/065,792, filed Nov. 14, 1997.

BACKGROUND OF THE INVENTION

1. Field of the Invention

This invention relates to a pilot valve suitable for use with a nebulizer which has high pressure gas delivered directly to the unit waiting for utilization.

2. Description of the Previously Published Art

A problem with previous nebulizer operation has recently been recognized as very important to the proper administrations of fluid drugs and medicaments by the aerosol or nebulized mode of administration. Previously, nebulization of medication to obtain the desired particle sizes and density has been continuously delivered to the patient throughout both the inhalation and exhalation phases of a breathing cycle. This led to merely approximating the dosage actually delivered during the critical period of inhalation. Variations in the length of the phases of the breathing cycle would defeat proper dosage based on these approximations. Likewise, intermittent nebulization which is patient controlled or by a metered dose inhaler requires a degree of coordination not necessarily present in a patient requiring the treatment either by condition of age or the severity of illness. Further, where intermittent nebulization is provided by sensing the negative pressure of patient inhalation and using that sensing to trigger or initiate high pressure gas flow, the gas, i.e., air or oxygen, which is stored under pressure is normally maintained at some distance for the nebulizer unit. When the system detects that the patient is inhaling, the valve at the gas source is opened and there is some delay before the gas reaches the nebulizer unit. This delay is due to several factors including the length of the delivery tube, the inside diameter of the tubing, the pressure being used and the compressibility of the gas.

These factors result in a delay in delivery which is a patient compliance problem because the system may be delivering medication for an indeterminate interval of the inhalation cycle.

Without knowing when in the inhalation cycle the delivery has begun, there is no way of knowing how much medicament has been utilized. This is exacerbated by the fact that the high pressure gas when finally reaching the nebulizer is not at the steady pressure state needed by the system in order to provide the proper particle size and density. The optimum size and density should be inhaled at the critical time, i.e., as near as possible to the start of inhalation. Only by achieving this can the proper concentration of medicament and, therefore, the proper dosages be prescribed with the confidence that the patient will receive the prescribed dosage in the form and amount necessary for complete effective utilization by the patient without waste and possibly contamination of the local environment where the nebulizer is exhausting into the surrounding air as during continuous nebulization.

3. Objects of the Invention

It is, therefore, an object of this invention to provide a valve designated herein as a pilot immediately adjacent the nebulizer gas inlet which has the high pressure gas supplied directly to the pilot valve so that when the valve is opened in response to system determinations, the gas at high pressure can be substantially immediately delivered at a steady state of flow and pressure to the nebulizer unit to nearly or substantially instantaneously begin nebulization producing the proper distribution range and of particle sizes at the desired density.

These and further objects of the invention will become apparent as the description of the invention proceeds.

SUMMARY OF THE INVENTION

A pilot valve has been designed which permits the delivery of relatively high pressure gas on the order of 20–50 psi directly from the valve. The valve has a housing with an outlet gas delivery tube for the relatively high pressure gas to flow immediately to a connected nebulizer. A poppet valve is positioned in the gas delivery tube and has a valve stem which is spring loaded to maintain the valve in the closed position. The high pressure gas is delivered by tubing to the seat of the closed poppet valve. A trigger gas, in the form of a low pressure gas, is supplied to the diaphragm of the pilot valve to cause the pilot valve to open. The pilot valve has a further poppet valve opening mechanism which responds to the presence of the trigger gas to move the valve stem of the poppet valve to open the poppet valve. With the poppet valve open the high pressure gas passes through the poppet valve and through the pilot valve. In the preferred embodiment this opening mechanism is a diaphragm which moves in response to the trigger gas and causes a backup disk to also move and force a piston against the valve stem of the poppet valve to open the poppet valve.

BRIEF DESCRIPTION OF THE DRAWINGS

FIG. 1 is plan view of the pilot valve.

FIG. 2 is an exploded view of the pilot valve.

FIG. 3*a* is a cross-sectional view of the pilot valve when the valve is open.

FIG. 3*b* is a cross-sectional view of the pilot valve when the valve is closed.

DESCRIPTION OF THE PREFERRED EMBODIMENTS

The pilot valve assembly 10 is shown in FIG. 1 where the pilot valve 12 has an oxygen supply inlet 14 for receiving oxygen under a relatively high pressure of about 20 to 50 psi from oxygen supply line 18. The opening of the valve is controlled in response to a trigger gas under low pressure in line 24 which connects to the pilot valve via sense line inlet 20.

The relationship of the component parts of the pilot valve are illustrated in the exploding view shown in FIG. 2. The bottom cover plate 30 has an internal central portion with an internal rim 32 which is surrounded by an annular ring 34. Within the internal rim 32 is the bottom plate 38 which has an opening 22 from the sense line inlet 20 (not shown). Within the outer annular ring 36 is an outer annular internal surface 40 which has opening 16 from the oxygen supply inlet 14.

Spaced above the bottom plate is the diaphragm 42 and a backup disk 44. Above these disks is a disk holder unit 50. This unit has a central disk holder 52 which is held in the central position by three support arms 54. One of these arms 56 is reinforced since it has an opening 58 through which the high pressure oxygen gas is being supplied to the valve. The central core 60 has an opening 62 for a piston 70. Spaced above this unit in the exploded view is the piston 70 which will slide into the opening 60. Above the piston is a poppet valve assembly 80 made up of a valve stem 82 which extends through the valve, a threaded base portion 84 of the valve, a valve housing 86 which is preferably made of an elastomeric material and the valve 88. Above the poppet valve is top cover plate 100 which has a central oxygen delivery tube 102 with an opening 104 within the tube.

Figure 3A:
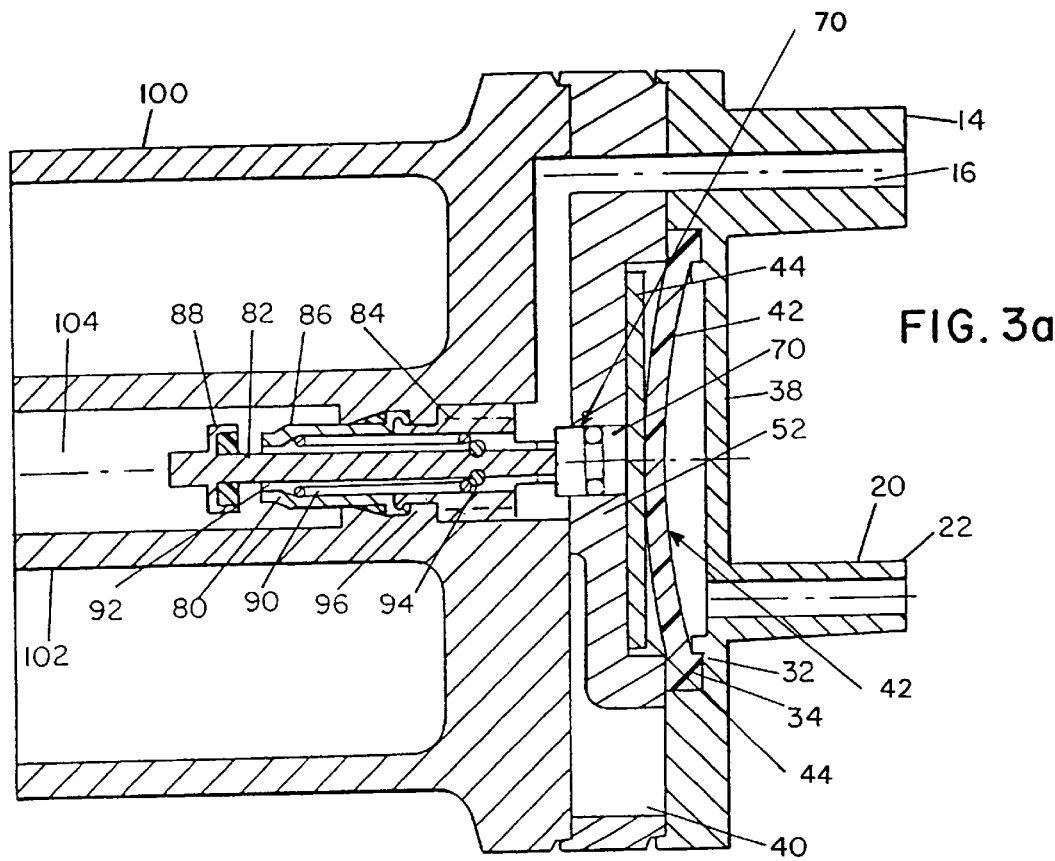
Figure 3B:
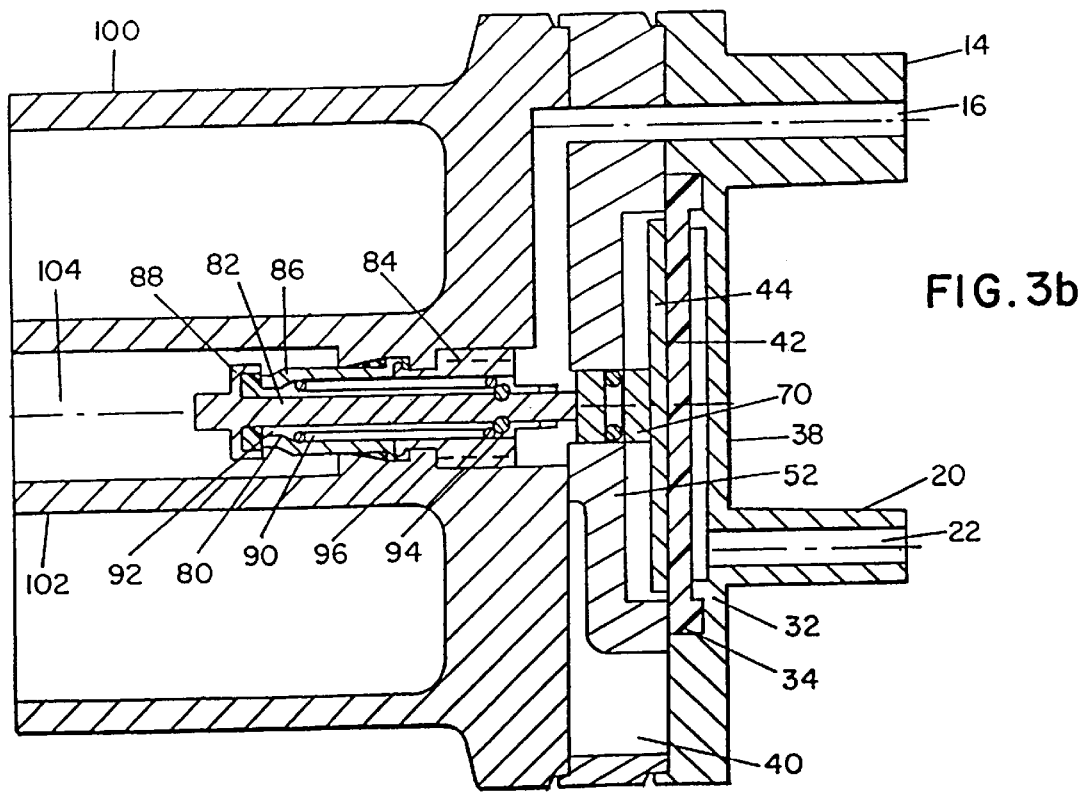

The relationship between the parts is further seen in the cross-sectional view in FIG. 3*a* where the valve is open and in FIG. 3*b* where the valve is closed.

In FIG. 3*a* the relationship between the diaphragm and the poppet valve is shown. In this view trigger gas has entered the opening 22 in the sense line inlet 20 and pushed the diaphragm 42 in contact with the backup disk 44. The backup disk has moved the piston 70 to the left where it engages the valve stem 82 and in turn moves the valve stem to the left. An opening forms between the valve 88 and the left end of the valve housing 86. Through this opening the oxygen under pressure can now pass. This oxygen enters the pilot valve through opening 16 in the oxygen supply inlet 14 and it flows around the valve stem 82 in the annular passageway 92 between the valve stem 82 and the valve housing 86 in the region where the internal spring 90 is positioned.

FIG. 3*a* illustrates further preferred structural features. The internal rim 32 on the inside of bottom plate 38 forms an annular ring region 34 where a portion of the diaphragm is in snap-fit engagement to hold the diaphragm in place. The poppet valve is held in place by the threaded portion 84 and the expanded portion of the valve housing 86 abuts against the shoulder 96 in the central oxygen delivery tube 102.

FIG. 3*b* is the same cross-sectional view of the pilot valve assembly, but when the valve is closed. In the normal closed condition, the internal spring 90 within the poppet valve is in compression and is pushing from the left end of the valve housing 86 against the expanded region 94 on the valve stem 82. This causes the valve stem 82 to push the piston 70 back to the far right position in the central disk holder 52. The piston 70 will move back to this position on the right side because there is no trigger gas flowing into the opening 22 in the sense line inlet 20. The diaphragm is in its flat upright position as shown in FIG. 3*b*. The backup plate is also next to it on the right side and away from the central disk holder 52. With the valve stem being forced to the right by the spring 90, the poppet valve 88 is forced in a closed position in an abutting relationship with the left end of the valve housing 86 so the valve is closed.

The response time of the pilot valve may be optimized by selecting the length and internal diameter of the pilot line to insure the desired response. Likewise, the pressure sensing equipment or apparatus can include sensing pressure differentials to characterize the duration of the exhalation cycle and provide for a trigger of the flow of control gas to the pilot valve to start the flow of nebulization gas to the nebulizer near the end of the exhalation cycle as described in U.S. Pat. No. 5,626,131, U.S. Pat. No. 5,666,945 and U.S. application Ser. No. 08/480,353, filed Jun. 7, 1995, which are incorporated herein by reference in their entirety. The sensing may be solely of the beginning of inhalation as is done by several commercially available pressure sensing units, to start the flow of the control gas to the pilot valve. Likewise, the available units can be modified to provide for a sufficient interval of time of application of the control gas to the pilot valve for the higher pressure driving gas to deliver pre-selected amounts of pre-selected concentrations of fluid medicament by aerosol from the attached nebulizer.

Any of a wide variety of patient interfaces for the sensing may be provided including nasal cannulae, either divided or not or mouthpieces attached to T-shaped tubes to which the nebulizer is attached. In the art such a device is described in U.S. Pat. No. 4,396,015 and U.S. Pat. No. 5,570,682, which are also incorporated herein by reference in their entirety. Further, adaptors fitted in one opening of the T-shaped connector may be employed which will provide a tubing connection to the selected pressure sensing apparatus for activating the supply of control gas to the pilot valve. Such adaptors and the like or other breathing circuit components may be supplied that will permit, inhalation of air as well as nebulized medication and either exhaust exhalation gases or operate to permit the exhaust through other one-way valves in the breathing circuit.

The nebulizer shown in U.S. Pat. No. 5,584,285 can be employed with a connected sense tube as shown therein to control pilot valve operation adjacent the inlet of the nebulizer where inhaled air enters from the top of the nebulizer to assist the flow of nebulized medication to the patent through the mouthpiece while exhaled air will be exhausted through the mouthpiece. This patent is also incorporated by reference in its entirety.

It is understood that the foregoing detailed description is given merely by way of illustration and that many variations may be made therein without departing from the spirit of this invention.

What is claimed is:

1. A nebulizer gas supply control valve for controlling the supply of a gas to a nebulizer comprising a) a housing having a gas delivery tube (102);

b) a poppet valve (80) in the gas delivery tube having a valve stem (82) which is biased by a spring (90) to maintain the valve closed;

c) a high pressure gas supply inlet (16) for providing relatively high pressure gas to the poppet valve;

d) a trigger gas supply inlet (22) to provide relatively low pressure gas to the control valve; and e) a poppet valve opener (42,44), having a diaphragm isolated from the high pressure gas which responds to pressure applied by the trigger gas to move the valve stem of the poppet valve to open the poppet valve whereby the relatively high pressure gas passes through the poppet valve and thereby through the control valve, wherein the poppet valve opener comprises the diaphragm (42), exposed on one face to the trigger gas supply inlet and, on an opposed face, to a closed chamber, which moves in response to applied trigger gas pressure, and a piston (70) unattached to the valve stem (82) and extending in a sealed manner from the closed chamber to move the valve stem whereby the trigger gas moves the diaphragm which in turn moves the piston and the valve stem to open the poppet valve;

wherein the poppet valve opener comprises a backup disk (44) which is separate and unattached to the diaphragm, and is located between the diaphragm and the piston, to convey the movement of the diaphragm to the piston.

2. A control valve according to claim 1, wherein the valve stem and piston are in contact with one another with the control valve both open and closed.

3. A control valve according to claim 1, wherein, the spring is located to act on the piston to oppose pressure exerted of the trigger gas on the diaphragm.

* * * * *